US 6,501,977 B1

(12) United States Patent
Kimmlingen

(10) Patent No.: US 6,501,977 B1
(45) Date of Patent: Dec. 31, 2002

(54) METHOD FOR OPERATING A MAGNETIC RESONANCE TOMOGRAPHY DEVICE

(75) Inventor: Ralph Kimmlingen, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 237 days.

(21) Appl. No.: 09/712,276

(22) Filed: Nov. 15, 2000

(30) Foreign Application Priority Data

Nov. 16, 1999 (DE) .......................................... 199 55 117

(51) Int. Cl.$^7$ ................................................ A61B 5/055
(52) U.S. Cl. ........................ 600/410; 324/307; 324/309; 600/407
(58) Field of Search ................................. 600/407, 410; 324/307, 309

(56) References Cited

U.S. PATENT DOCUMENTS

| | | |
|---|---|---|
| 4,644,277 A | 2/1987 | Kunz |
| 4,670,716 A | 6/1987 | Kunz |
| 4,916,395 A | 4/1990 | Usui |
| 4,939,462 A | 7/1990 | Maeda et al. |
| 4,959,613 A | 9/1990 | Yamamoto et al. |
| 5,025,217 A * | 6/1991 | Van Vaals .................... 324/322 |
| 5,309,107 A | 5/1994 | Pausch |
| 5,512,828 A * | 4/1996 | Pausch et al. ............... 324/309 |
| 5,736,858 A | 4/1998 | Katznelson et al. |
| 6,418,336 B1 * | 7/2002 | Kimmlingen et al. ........ 600/410 |

OTHER PUBLICATIONS

"Peripheral Nerve Stimulation by Time–Varying Magnetic Fields," Abart et al, J of Computer Assisted Tomography, vol. 21, No. 4 (1997) pp. 532–538.

* cited by examiner

Primary Examiner—Marvin M. Lateef
Assistant Examiner—Runa Shah Qaderi
(74) Attorney, Agent, or Firm—Schiff Hardin & Waite

(57) ABSTRACT

In a method for operating a magnetic resonance tomography device having a gradient system, which contains at least one gradient coil arrangement for generating a gradient field in a spatial direction and which also contains an energy supply device that is connected to the gradient coil arrangement, and wherein the gradient coil arrangement has at least one first sub-coil and one second sub-coil, and wherein the energy supply device is fashioned such that currents can be adjusted independently of one another in the sub-coils for the continuous adjustment of at least one property of the gradient field, the current in at least one of the sub-coils is determined and adjusted by solving an optimization task containing a target function and at least one secondary condition so that stimulations of a living examination subject are avoided.

24 Claims, 7 Drawing Sheets

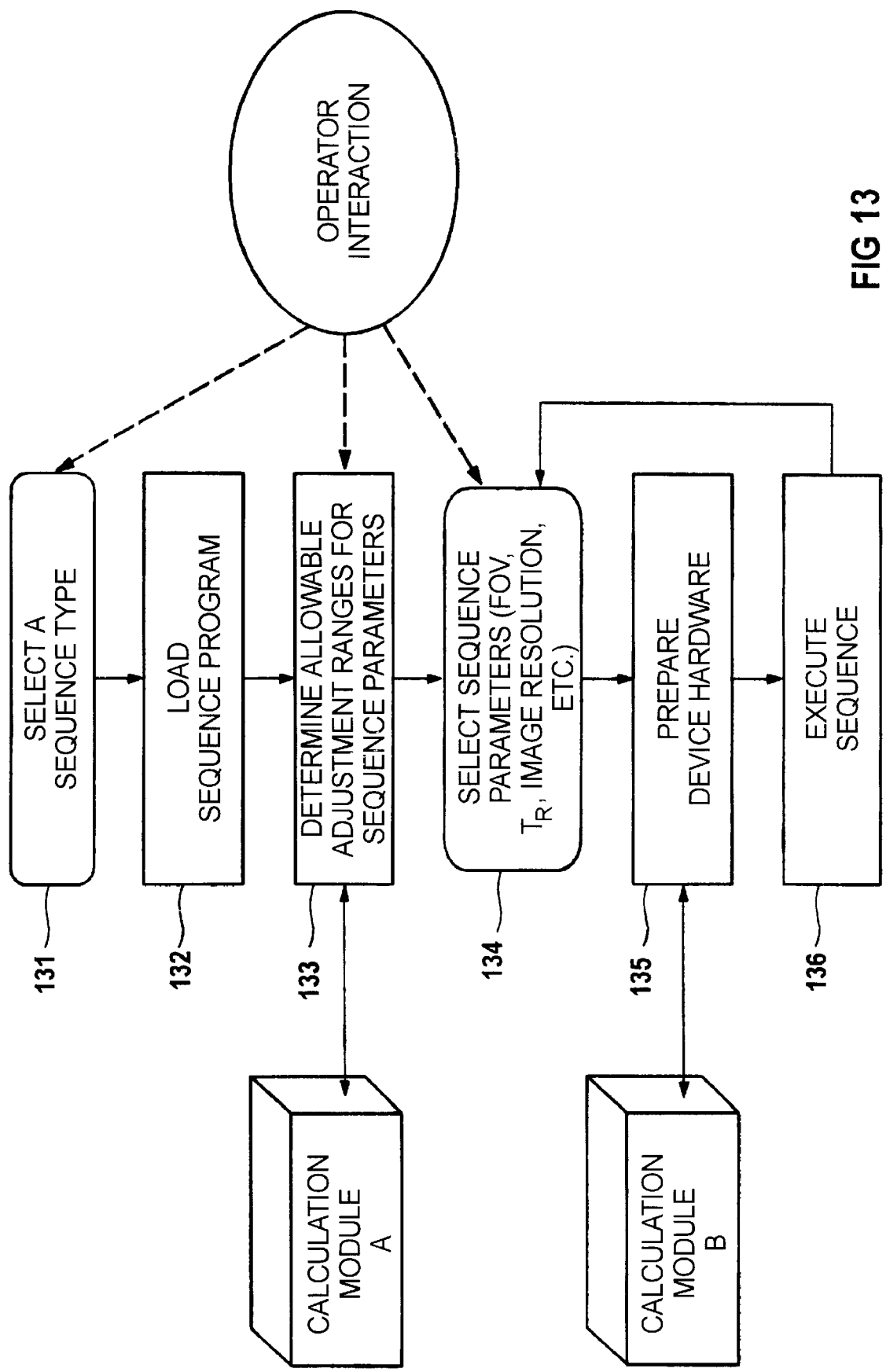

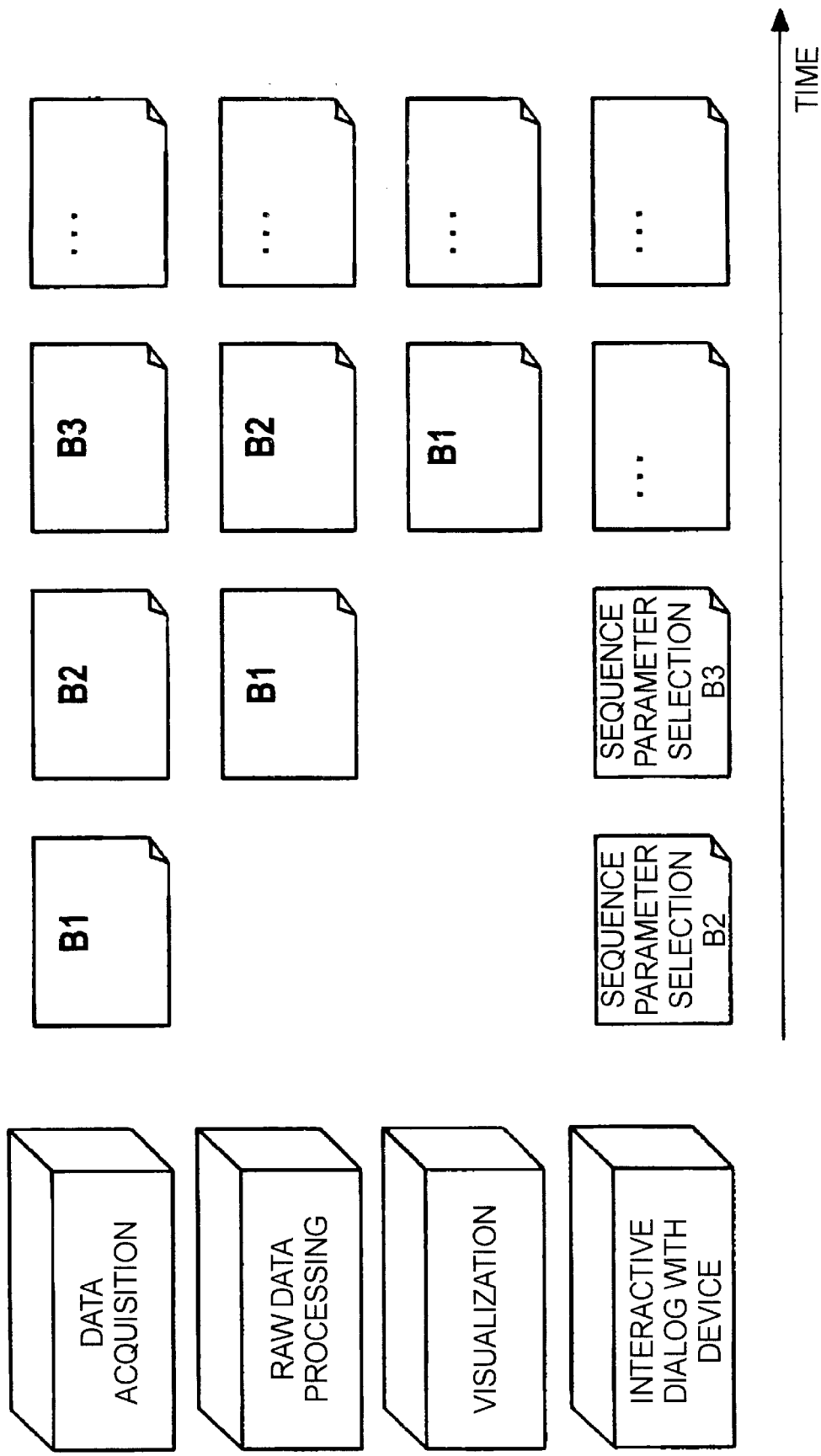

METHOD FOR OPERATING A MAGNETIC RESONANCE TOMOGRAPHY DEVICE

BACKGROUND OF THE INVENTION

1. Field of the Invention

The present invention relates to a method for operating a magnetic resonance tomography device with a gradient system having at least one gradient coil arrangement for generating a gradient field in a spatial direction and which contains an energy supply device that is connected to the gradient coil arrangement; the gradient coil arrangement having at least one first sub-coil and one second sub-coil, and wherein the energy supply device is fashioned such that the currents in the sub-coils can be adjusted independently of one another.

2. Description of the Prior Art

Magnetic resonance tomography is a known technique for acquiring images of the inside of the body of a living examination subject. For this purpose, rapidly switched magnetic gradient fields, which have a high amplitude and which are generated by a gradient system, are superimposed on a static basic magnetic field.

The gradient system includes gradient coils, gradient amplifiers and a gradient control. One of the gradient coils, for a specific spatial direction, generates a gradient field having a gradient, which, at least within an imaging volume of the magnetic resonance tomography device, is approximately of the same magnitude in a location-independent manner at any arbitrary point in time. Since the gradient field is a chronologically variable magnetic field, the aforementioned is still valid for any point in time but the magnitude is variable from one point in time to another point in time. Normally, the direction of the gradient is strictly prescribed by the gradient coil design.

The currents are adjusted in the gradient coil for generating the gradient field. The amplitudes of the required currents amount to several 100 A. The current rising and falling rates ("slew rate") amount to several 100 kA/s. The gradient coil is connected to a gradient amplifier for the current supply. Since the gradient coil represents an inductive load, high initial voltages of the gradient amplifier are necessary for generating the aforementioned currents.

In the case of magnetic resonance image pickups in living examination subjects, unwanted stimulations in the examination subject can be triggered due the switching of the gradient fields. The gradient fields thereby have an effect on the examination subject and are characterized by a chronologically changing magnetic flux density, which generates eddy and inductance currents in the examination subject.

Methods are known for predicting these stimulations. One of these methods for monitoring the stimulation is based on the dB/dt model, for example. In this method, the values of the chronological change of the magnetic flux density (dB/dt-values) of gradient fields are controlled and monitored, these values occurring during magnetic resonance tomography. The maximally allowable dB/dt values derive from the result of a stimulation study with the corresponding gradient coil, or from the limiting values that are strictly prescribed by the facility operating the tomography apparatus, for example. Further details are provided by J. Abart et al. "Peripheral Nerve Stimulation by Time-Varying Magnetic fields", J. Computer Assisted Tomography (1997) 21 (4), pages 532 to 538.

The initiation of stimulations essentially depends on the type of pulse sequence employed in the imaging. Such sequences are broadly differentiated between conventional sequences and the fast sequences. Normally, conventional sequences require a high linearity of the gradient fields within a specific linearity volume, for example a linearity of approximately 5% in a spherical linearity volume having a diameter of approximately 40 to 50 cm given moderate gradient intensities of 10 to 20 mT/m and switching times of approximately 1 ms. High gradient intensities, e.g. 20 to 40 mT/m, are extremely rapidly switched for the fast sequences (switching times circa 100 to 500 $\mu$s). The time-varying magnetic flux density of the gradient fields induces electric currents in the examination subject, and these electric currents can initiate stimulations of the examination subject. As a result of faster time variations, i.e., faster switching times and higher values of the magnetic flux density of gradient fields, the induced currents become larger and the likelihood of stimulations increases. Values that are the largest in terms of magnitude are reached at the edges and outside of the linearity volumes; this is where the maximal field boost occurs. Given the requirements to be met by the gradient intensity and the switching time, the boost is reduced and therefore the risk of stimulation because a gradient coil having a smaller linearity volume is utilized. Therefore, the linearity volume is reduced to a diameter of 20 cm, for example, in fast sequences. Normally, a gradient coil with the aforementioned properties for fast sequences is not suitable for conventional whole body applications, but it is suitable for magnetic resonance imaging techniques, such as the echo planar method and its hybrids.

Published German application OS195 40 746 describes a modular gradient coil system, which has two gradient coils for a spatial direction. One of the two coils or a series connection of both gradient coils is optionally connected to a gradient amplifier. For example, only one of the gradient coils is used for fast sequences and the series connection is used for conventional sequences. The gradient coil system thereby has a small linearity volume for fast sequences and allows the fast switching of gradient fields with large gradient intensities. Given the common operation of both coils, the gradient coil system has a larger linearity volume for conventional sequences with slowly switched gradient fields and with respect to smaller gradient intensities. A disadvantage of the aforementioned gradient coil system is that the size of the linearity volume and the quality of the linearity can be varied only in three steps at a maximum.

SUMMARY OF THE INVENTION

It is an object of the present invention to provide a method for operating a magnetic resonance tomography device of the type described above which improves the avoidance of producing stimulations of a living examination subject.

This object is achieved in accordance with the invention in a method for operating a magnetic resonance tomography device having a gradient system, which contains at least one gradient coil arrangement for generating a gradient field in a spatial direction and which contains an energy supply device that is connected to the gradient coil arrangement, wherein the gradient coil arrangement has at least one first sub-coil and one second sub-coil and wherein the energy supply device is fashioned such that currents can be adjusted independently of one another in the sub-coils, and wherein, for the continuous adjustment of at least one property of the gradient field, the current in at least one of the sub-coils is determined and adjusted by solving an optimization task containing a target function and at least one secondary condition, so that stimulations of a living examination subject are avoided.

For example, stimulations are prevented when an extreme value of the magnetic flux density of the gradient field remains below a fixable stimulation limiting value given a fixed slew rate of a sequence. The optimization task is solved by a variation calculation, for example. The target function contains coefficients of a spherical function development of a magnetic flux density of the gradient field, and the target function contains coefficients for each of the sub-coils. The coefficients for one of the sub-coils are multiplied with a factor that corresponds to a ratio of an adjustable current to a nominal current of the sub-coil. For example, a further secondary condition is that at least one of the coefficients multiplied with the factor is larger than a fixed limiting value. For example, it is possible to prescribe a minimally required gradient intensity with this version of the invention.

In addition to a current adjustment for operating the gradient system, a design of the gradient system also can be determined by solving the aforementioned optimization task. In the design of the gradient coil arrangement, coefficients and necessary nominal currents of the sub-coils are determined from properties of the gradient field prescribed in areas, in combination with other design criteria such as rigid body movement of the gradient coil arrangement in the device, eddy current behavior, noise generation etc. On the basis of a fixed gradient coil arrangement with fixed coefficients and nominal currents, the currents to be adjusted are determined dependent on the desired properties of the gradient field by means of the determination of current adjustments.

In an embodiment, at least one of the sequence parameters is prescribed for a selected sequence type in an area, so that the sequence can be executed by means of the gradient system of the device. The sequence parameter thereby co-determines at least one of the properties of the gradient field. For example, the minimally required gradient intensity and the minimally required slew rate is fixed in that a sequence type is selected. Furthermore, the selection of a field of views, for example, directly effects the size of the linearity volume. Since the user can only select parameters that can be executed by means of the gradient system of the device, the prescription of parameters that cannot be executed is avoided.

In another embodiment, the sequence parameter can be varied during the execution of the sequence.

In another embodiment, a current effecting a first linearity and/or a first linearity volume and/or a first gradient intensity of the gradient field is adjusted in the first sub-coil, and the current in the second sub-coil is controlled such that the first linearity and/or the first linearity volume and/or the first gradient intensity can be continuously varied. The current in the second sub-coil can be controlled for the purpose as to size and polarity sign.

In another embodiment, the currents are adjusted in the sub-coils such that stimulations of a living examination subject are prevented. Since the properties of the gradient field can be continuously adjusted at least in most areas, it is possible in an adjustment that avoids stimulations to always remain slightly below a stimulation threshold, so that the gradient system is operated with optimum efficiency.

In another embodiment, the energy supply device contains a first gradient amplifier, which is connected to the first sub-coil, and a second gradient amplifier, which is connected to the second sub-coil. As a result of the utilization of known and proven components of a magnetic resonance tomography device, the energy supply device is fashioned in a simple way such that the currents in the sub-coils can be adjusted independently of one another.

In another embodiment, the first sub-coil is fashioned for a specific linearity volume of the gradient field and/or for a specific linearity of the gradient field, and the second sub-coil is fashioned as a correction coil, so that the specific linearity volume and/or the specific linearity can be varied. As a result, the specific linearity volume can be enlarged and the specific linearity can be improved via the linearity volume for conventional sequences, in particular. The linearity volume, which is spherical for example, is the volume within which the linearity of the gradient field does not exceed a fixed linearity deviation, indicated in percent, for example. Therefore, the linearity of the gradient field characterizes the quality of the gradient field within the linearity volume, whereby the quality is described by the linearity deviation. A linearity deviation of 0% means that the curve of the gradient field is ideally linear within the linearity volume.

In another embodiment, the first sub-coil is fashioned for a specific gradient intensity of the gradient field, with the gradient intensity preferably being the maximum gradient intensity in terms of magnitude for the first sub-coil, and the second sub-coil is fashioned as an amplification coil, so that the specific gradient intensity can be varied, preferably increased. Therefore, the high gradient intensities that are particularly necessary for the fast sequences can be reached.

DESCRIPTION OF THE DRAWINGS

FIG. 13 is a flow chart of a sequence in a device with continuously adjustable gradient field properties in accordance with the invention.

FIG. 14 illustrates a pipeline architecture of a realtime sequence in accordance with the invention.

DESCRIPTION OF THE PREFERRED EMBODIMENTS

Figure 1:
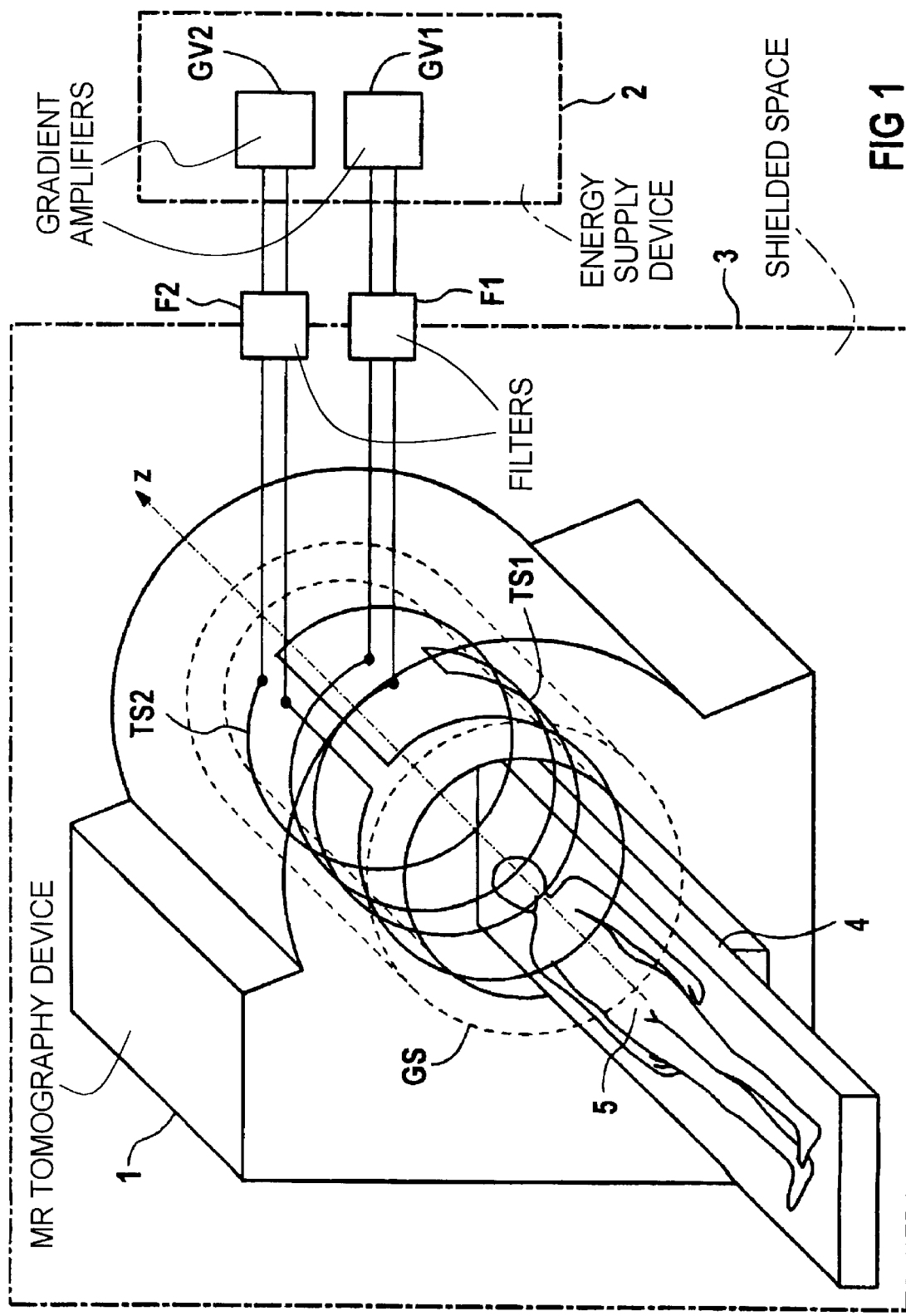
FIG. 1 is a block diagram of a magnetic tomography device with a gradient system, operable in accordance with the invention.

FIG. 1 shows a magnetic resonance tomography device 1 with a gradient system. The gradient system includes a gradient coil system GS arranged in the device 1 and an energy supply device 2 that is connected to the gradient coil system GS. The gradient coil system GS contains a gradient coil arrangement for generating a gradient field in a spatial direction. For this purpose, a longitudinal gradient coil for generating a gradient field is shown in the z-direction as an example. For clarity, further gradient coils for generating gradient fields are not shown in further spatial directions, nor are shielding coils, as are usually present in a secondary plane. The gradient coil arrangement has a first sub-coil TS1 and a second sub-coil TS2.

The device 1 has a movable bearing device 4 supporting a patient 5 to be examined. The actual device 1 including the gradient coil system GS is arranged in a shielded space 3. The energy supply device 2 is arranged outside of the shielded space 3 and contains a first gradient amplifier GV1, which is connected to the first sub-coil TS1, as well as a second gradient amplifier GV2, which is connected to the second sub-coil TS2. The connections between the sub-coils TS1 and TS2 and the gradient amplifiers are fed into the shielded space 3 via respective filters F1 and F2. As a result of the aforementioned fashioning of the energy supply device 2 with two gradient amplifiers GV1 and GV2, the currents in the sub-coils TS1 and TS2 can be adjusted independently of one another. In the energy supply device 2, further gradient amplifiers (not shown) are provided for the further gradient coils.

Only a few turns of the sub-coil TS1 and TS2 are shown as examples. In different embodiments, not only sub-coils TS1 and TS2, that are spatially separated from one another, but also sub-coils TS1 and TS2 that are interleaved with one another are possible. In order to exactly determine the arrangement of all turns of the gradient coil arrangement, an optimization method is used as described in German OS 42 03 582, for example.

In an embodiment, the sub-coil TS1 and TS2 have the same inductance. Therefore, the two gradient amplifiers GV1 and GV2 can be identically fashioned given equal minimal current rising times in the sub-coils TS1 and TS2.

Figure 2:
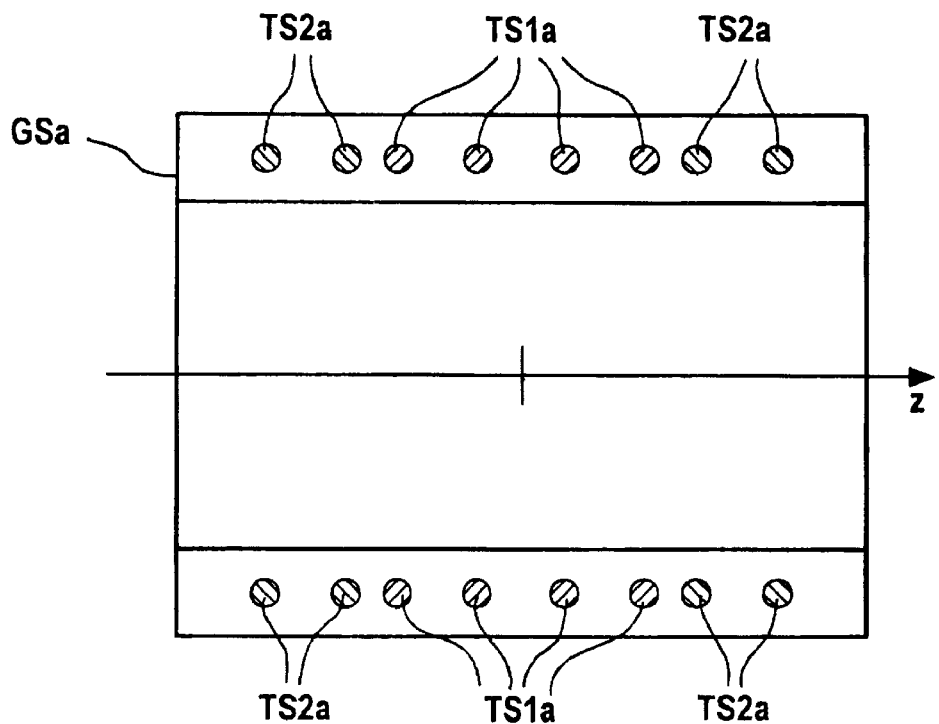
FIG. 2 is a longitudinal section of a gradient coil system with a first sub-coil and a second sub-coil for generating a gradient field with an adjustable linearity and/or with an adjustable linearity volume, in accordance with the invention.
Figure 6:
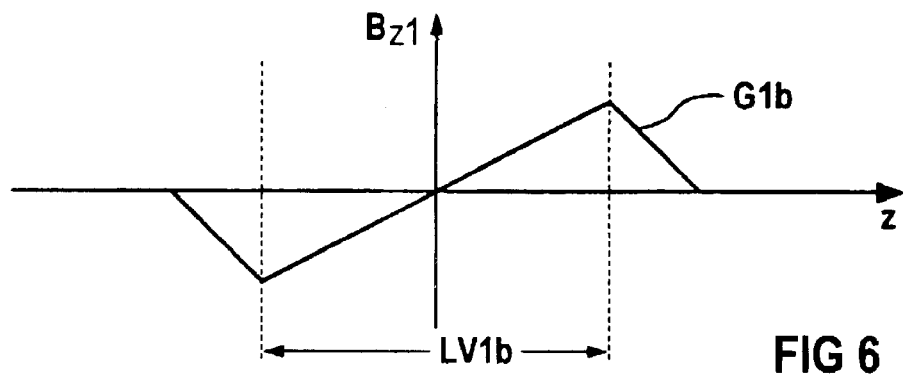
FIG. 6 is an idealized curve of the magnetic flux density of a gradient field generated by the first sub-coil of FIG. 2, in accordance with the invention.
Figure 7:
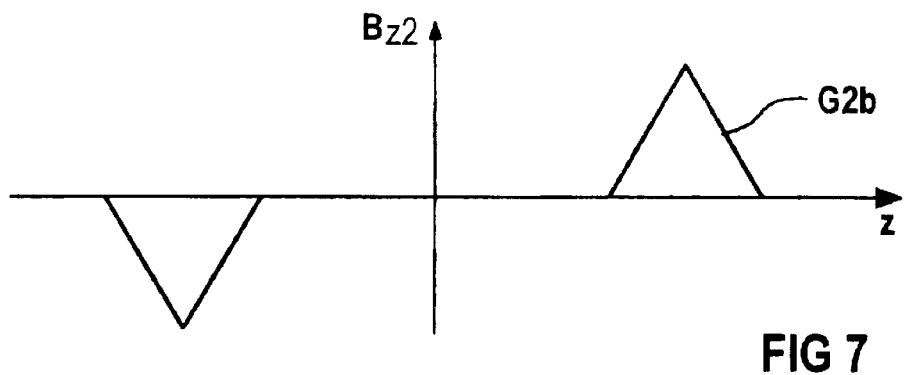
FIG. 7 is an idealized curve of the magnetic flux density of a gradient field generated by the second sub-coil of FIG. 2, in accordance with the invention.
Figure 8:
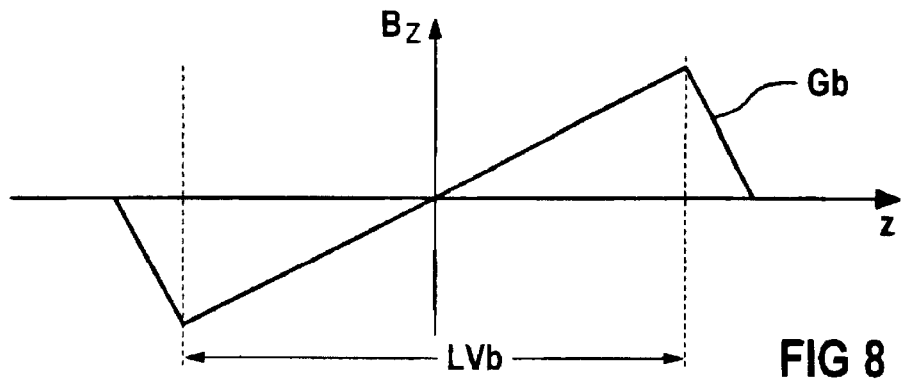
FIG. 8 is an idealized curve of the magnetic flux density of a gradient field generated by both sub-coils of FIG. 2, in accordance with the invention.

FIG. 2 shows a longitudinal section through a hollow cylindrical gradient coil system GSa. A principal axis of the hollow cylinder defines the z-direction. The gradient coil system GSa contains a longitudinal gradient coil arrangement for generating a gradient field in the z-direction. The gradient coil arrangement has a first sub-coil TS1$a$ and a second sub-coil TS2$a$. The conductors of both sub-coils TS1$a$ and TS2$a$ are arranged in the same winding plane and are designated corresponding to the sub-coils TS1$a$ and TS2$a$. Only a few conductors of the gradient coil arrangement are shown as examples. The second sub-coil TS2$a$ is fashioned as a correction coil with respect to the first sub-coil TS1$a$. In an embodiment, the correction coil TS2$a$ is fashioned such that a linearity of the gradient field can be varied (as shown in FIGS. 3 to 5) or is fashioned in a further embodiment such that a linearity volume of the gradient field can be altered (as shown in FIGS. 6 to 8).

Figure 3:
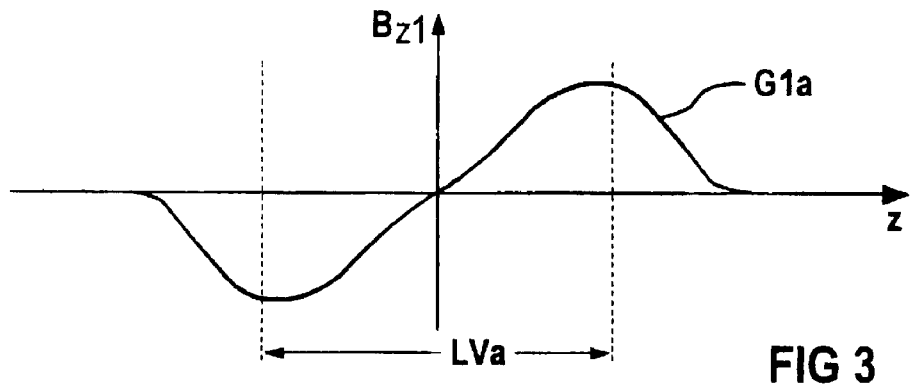
FIG. 3 is a curve of the magnetic flux density of a gradient field generated by the first sub-coil of FIG. 2, in accordance with the invention.

FIG. 3 shows a curve G1$a$ of the magnetic flux density $B_{z1}$ of a gradient field along the z-axis, which is generated by the first sub-coil TS1$a$ given a corresponding current in the first sub-coil TS1$a$ of FIG. 2. The aforementioned gradient field thereby exhibits a specific linearity in a selected linearity volume having the diameter LVA along the z-axis. An optimal linearity or a linearity deviation of zero is reached when the curve of the gradient field within the linearity volume is a straight line. The linearity deviation of the gradient field generated by the first sub-coil TS1$a$ is situated within the 5% range, for example.

Figure 4:
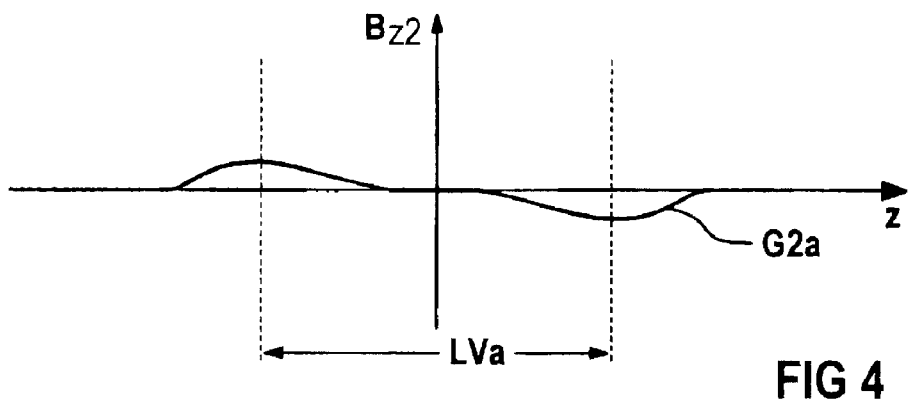
FIG. 4 is a curve of the magnetic flux density of a gradient field generated by the second sub-coil of FIG. 3, in accordance with the invention.

FIG. 4 shows a curve G2$a$ of the magnetic flux density $B_{z2}$ of a magnetic field along the z-axis, which is generated by the correction coil TS2$a$ given a corresponding current in the correction coil TS2$a$.

Figure 5:
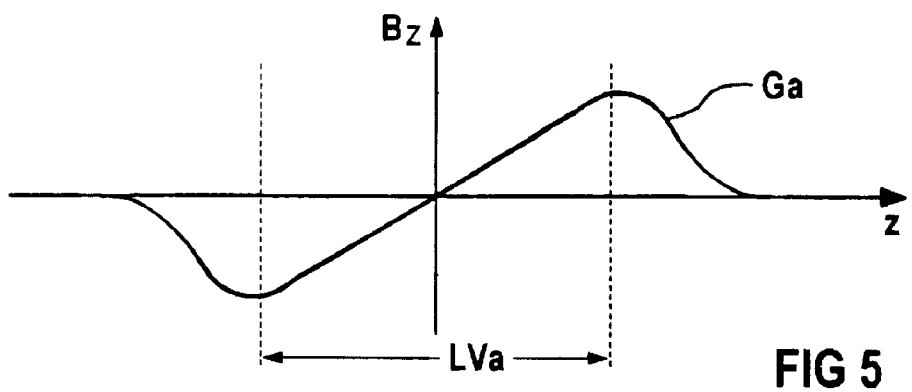
FIG. 5 is a curve of the magnetic flux density of a gradient field generated by both sub-coils of FIG. 2, in accordance with the invention.

FIG. 5 shows a curve Ga of the magnetic flux density $B_z$ of a resulting gradient field along the z-axis, which curve arises as a result of the superimposition of the curve G1$a$ of FIG. 3 with respect to the curve G2$a$ of FIG. 4. As a result of the superimposition of the gradient field generated by the first sub-coil TS1$a$ with respect to the magnetic field generated by the correction coil TS2$a$, the linearity of the resulting gradient field compared to the unchanged linearity volume can be improved relative to the gradient field that is exclusively generated by the first sub-coil TS1$a$. The linearity can be continuously adjusted at least in most areas by adjusting the currents in the sub-coils TS1$a$ and TS2$a$.

FIG. 6 shows an idealized curve G1$b$ of the magnetic flux density $B_{z1}$ of a gradient field along the z-axis, which is generated by the first sub-coil TS1$a$ in the first sub-coil TS1$a$ of FIG. 2 given a corresponding current. The aforementioned gradient field exhibits a fixed linearity volume having a diameter LV1$b$ along the z-axis and has a specific gradient intensity.

FIG. 7 shows an idealized curve G2$b$ of the magnetic flux density $B_{z2}$ of a magnetic field along the z-axis, which is generated by the correction coil Ts2$a$ given a corresponding current in the correction coil TS2$a$ of FIG. 2.

FIG. 8 shows an idealized curve Gb of the magnetic flux density $B_z$ of a resulting gradient field along the z-axis, which curve arises as a result of the superimposition of the curve G1b of FIG. 6 with respect to the curve G2$b$ of FIG. 7. As a result of the superimposition of the gradient field generated by the first sub-coil Ts1$a$ with respect to the magnetic field generated by the correction coil TS2$a$, an enlarged linearity volume having the diameter Lvb can be adjusted relative to the linearity volume having the diameter LV1$b$ given an unchanged gradient intensity. The linearity volume can be continuously adjusted at least in most areas when the currents in the sub-coils TS$a$ and TS2$a$ are correspondingly adjusted.

Figure 9:
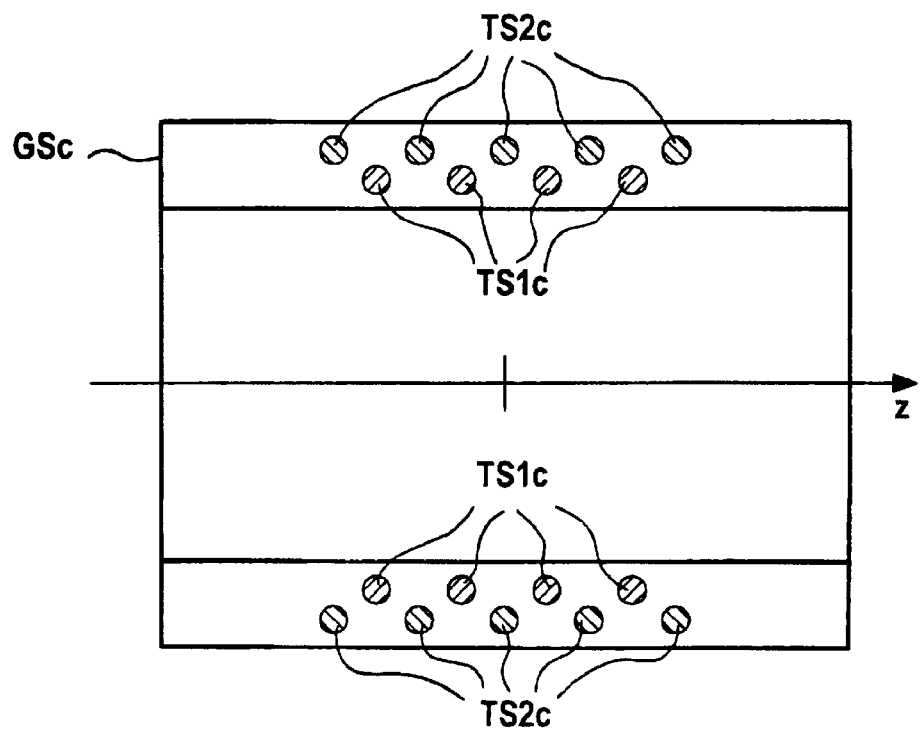
FIG. 9 is a longitudinal section through a gradient coil system with a first and a second sub-coil for generating a gradient field with an adjustable gradient intensity and linearity volume, in accordance with the invention.

FIG. 9 shows a longitudinal section through a hollow cylindrical gradient coil system GSc. A principal axis of the hollow cylinder defines a z-direction. The gradient coil system GSc contains a longitudinal gradient coil arrangement for generating a gradient field in the z-direction. The gradient coil arrangement has a first sub-coil TS1$c$ and a second sub-coil TS2$c$, whose conductors are correspondingly designated at the intersecting points. Only a few conductors of the gradient coil arrangement are shown as an example. The second sub-coil TS2$c$ is fashioned as an amplification coil for the first sub-coil TS1$c$. In contrast to FIG. 2, the conductors of the sub-coils TS1$c$ and TS2$c$ are arranged in different winding planes in FIG. 9.

Figure 10:
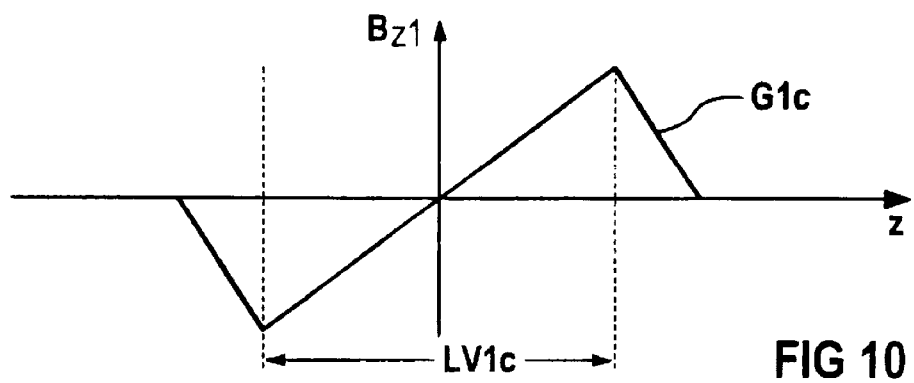
FIG. 10 is an idealized curve of the magnetic flux density of a gradient field generated by the first sub-coil of FIG. 9, in accordance with the invention.

FIG. 10 shows an idealized curve G1$c$ of the magnetic flux density $B_{z1}$ of a gradient field along the z-axis, which is generated with a maximal gradient intensity by the first sub-coil TS1c given a current in the amount of a rated current of the sub-coil TS1c of FIG. 9. The aforementioned gradient field thereby exhibits a specific linearity volume having a diameter LV1c along the z-axis. Furthermore, it is assumed in this example that the extreme values of the magnetic flux density $B_{z1}$ along the z-axis of the aforementioned gradient field are stimulation limiting values, which, if exceeded, causes stimulations in a living examination subject given a fixed slew rate.

Figure 11:
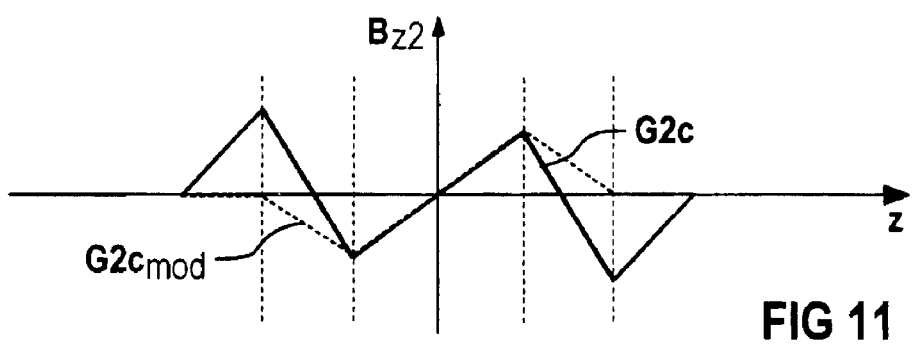
FIG. 11 is an idealized curve of the magnetic flux density of a gradient field generated by the second sub-coil of FIG. 9, in accordance with the invention.

A magnetic field that is generated by the amplification coil TS2c, by superimposition with respect to the gradient field generated by the first sub-coil TS1c, has the purpose of adjusting a resulting gradient field, which has a larger gradient intensity at least in a sub-area of the linearity volume having the diameter LV1c relative to the gradient field generated by the first sub-coil TS1c with maximum gradient intensity. With the condition of the fixed slew rate, which is unchanged for the resulting gradient field, extreme values of the magnetic flux density $B_z$ of the resulting gradient field are not to exceed the aforementioned extreme values of the magnetic flux density $B_{z1}$ so that the resulting gradient field does not lead to stimulations either. FIG. 11 shows an idealized curve G2c of the magnetic flux density $B_{z2}$ of the magnetic field along the z-axis, which is generated by the amplification coil TS2c given a corresponding current in the amplification coil TS2c of FIG. 9.

Figure 12:
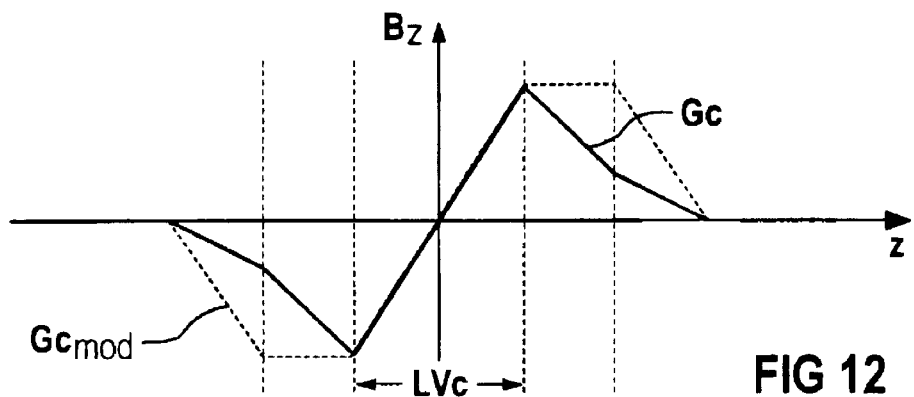
FIG. 12 is an idealized curve of the magnetic flux density of a gradient field generated by both sub-soils of FIG. 9, in accordance with the invention.

FIG. 12 shows an idealized curve Gc of the magnetic flux density $B_z$ of the resulting gradient field along the z-axis. This curve is derived from the superimposition of the curve G1c of FIG. 10 with respect to the curve G2c of FIG. 11. As a result of the superimposition of the gradient field generated by the first sub-coil TS1c with respect to the gradient field generated by the amplification coil TS2c, a larger gradient intensity can be adjusted relative to the maximal gradient intensity of the sub-coil TS1c given a reduced linearity volume having the diameter LVC. The gradient intensity of the resulting gradient field, within the linearity volume having the diameter LVc, is the sum of the gradient intensities of the fields generated by the sub-coils TS1c and TS2c. Therefore, a resulting gradient field having a larger maximal gradient intensity can be generated than is possible by means of one of the sub-coils TS1c or TS2c alone. The gradient intensity can be continuously adjusted by adjusting the currents in the sub-coils TS1c and TS2c.

Given the resulting gradient field, it should be noted that a reception of magnetic resonance signals by means of a high-frequency antenna, which is fashioned for the large linearity volume having the diameter LV1c, leads to falsifications of magnetic resonance images as a result of the smaller linearity volume having the diameter LVc. This is caused by undesired signal contributions from a difference volume between the linearity volume having the diameter LV1C and the linearity volume having the diameter LVc. The magnetic flux density $B_z$ of the resulting gradient field exhibits the same values within the difference volume as within the linearity volume with the diameter LVC.

Unfalsified magnetic resonance images, for example, are generated by using a high-frequency reception antenna, which is specifically adjusted to the linearity volume having the diameter LVC, for example, a switchable high-frequency reception antenna can be utilized or the amplification coil TS2c can be fashioned and powered such that the curves $G2c_{mod}$ and $Gc_{mod}$ of the flux density $B_{z2}$ and $B_z$ are generated for the fields in the FIGS. 11 and 12 (shown by dots).

In other embodiments, a gradient coil arrangement contains more than two sub-coils, or one of the sub-coils is fashioned such that it has an effect on a plurality of properties of a gradient field at the same time.

For example, a determination of currents to be adjusted with respect to the operation of the aforementioned gradient systems is based on a description of the magnetic flux density of a gradient field by a spherical function development, which is subsequently explained. The following can also be correspondingly applied for a design of aforementioned gradient coil arrangements.

The magnetic flux density B (r, θ, ϕ) of the gradient field of a gradient coil arrangement can be described by a spherical function development according to the following equations:

$$B(r, \theta, \varphi) = \sum_{l=0}^{\infty} \sum_{m=-l}^{+l} A_{(l,m)} \cdot r^l \cdot Y_{(l,m)}(\theta, \varphi) \text{ with}$$

$$Y_{(l,m)}(\theta, \varphi) = \begin{cases} P_{(l,m)}(\cos\theta) \cdot \cos(m\varphi) & m = 0, 1, 2, \ldots, l \\ P_{(l,|m|)}(\cos\theta) \cdot \sin(|m|\varphi) & m = -1, -2, \ldots, -l \end{cases}$$

wherein $A_{(l, m)}$ are the spherical coefficients with an appropriate scaling. Proceeding from an origin, the radius r and the angles ϕ and θ, as spherical coordinates describe a point in three-dimensional space. The origin is generally fixed in the center of the gradient coil arrangement. $P_{(l, m)}$ (cos θ) and $P_{(l, |m|)}$ (cos θ) are Legendre polynomial expansions or functions depending on cos θ.

Given a longitudinal spherical cylinder(jacket-shaped) gradient coil arrangement, merely coefficients $A_{(l, m)}$ with an uneven l and particularly with m=0 occur due to its properties of the symmetry for the magnetic flux density in the inside of the coil. Given a transverse spherical cylinder jacket-shaped gradient coil arrangement, merely the coefficients $A_{(l, m)}$ with an odd l and odd m are of importance due to its properties of symmetry. The following table, which contains the coefficients $A_{(l,m)}$ that are important in practical operation and their meaning with respect to the longitudinal and transversal gradient coil arrangement, makes this clear.

| longitudinal | transversal | meaning |
| --- | --- | --- |
| $A_{(1, 0)}$ | $A_{(1, 1)}$ | gradient field |
| $A_{(3, 0)}$ | $A_{(3, 1)}$; $A_{(3, 3)}$ | interference 3rd order |
| $A_{(5, 0)}$ | $A_{(5, 1)}$; $A_{(5, 3)}$, $A_{(5, 5)}$ | interference 5th order |
| $A_{(7, 0)}$ | $A_{(7, 1)}$; $A_{(7, 3)}$; $A_{(7, 5)}$; $A_{(7, 7)}$ | interference 7th order |
| $A_{(9, 0)}$ | $A_{(9, 1)}$; $A_{(9, 3)}$; $A_{(9, 5)}$; $A_{(9, 9)}$ | interference 9th order |

Apart from the coefficient $A_{(1,0)}$, all other coefficients $A_{(l, m)}$ are equal to zero for an ideal longitudinal gradient coil. Apart from the coefficient $A_{(1,1)}$, all other coefficients $A_{(l, m)}$ are equal to zero for an ideal transverse gradient coil.

In another embodiment according to FIG. 1, a longitudinal gradient coil has a first sub-coil and a second sub-coil. The first sub-coil is fed by a first gradient amplifier and the second sub-coil is fed by a second gradient amplifier, so that currents having a different amplitude and preceding sign can be adjusted independently of one another in the two sub-coils at the same time. The first sub-coil has a reference current $I_{n1}$ and the second sub-coil has a reference current $I_{n2}$. Depending on a current $I_1$ flowing at a specific point in time in the first sub-coil and depending on a current $I_2$ flowing at the same time in the second sub-coil, resulting coefficients $A_{(l,0)}$ for the longitudinal gradient coil derive from coefficients $A_{1(l,0)}$ for the first sub-coil and from coefficients $A_{2(l, 0)}$ for the second sub-coil according to the following equation:

$$A_{(l,0)} = \frac{l_1}{l_{n1}} \cdot A_{1(l,0)} + \frac{l_2}{l_{n2}} \cdot A_{2(l,0)}$$

The preceding equation for the longitudinal gradient coil with two sub-coils can be expanded to arbitrary gradient coils with an arbitrary number N of sub-coils:

$$A_{(l,m)} = \sum_{v=1}^{N} \frac{l_v}{l_{nv}} \cdot A_{v(l,m)}$$

Given a longitudinal gradient coil with two sub-coils, two basic embodiments of the second sub-coil are possible. A first sub-coil is used as a basis, with which a gradient field can be generated whose maximum gradient intensity is described by the coefficient $A_{1(1,0)}$.

In a first embodiment, the second sub-coil is fashioned as a correction coil according to FIG. 2, for example. A linearity and/or a linearity volume of the gradient field generated by the first sub-coil can be modified by means of the second sub-coil. Ideally, the coefficient $A_{2(1,0)}$ of the second sub-coil is equal to zero, since, as a pure correction coil, it is not to effect a change of the gradient intensity of the gradient field of the first sub-coil. For this purpose, its coefficients of higher order are fashioned such that they have a correcting effect on corresponding coefficients of the first sub-coil, so that the linearity and/or the linearity volume can be continuously adjusted at least in most areas for the gradient coil arrangement.

The aforementioned gradient coil arrangement, which is not actively shielded, can be mostly executed in a winding plane according to FIG. 2, for example. The reason for this is that the first sub-coil exhibits its largest conductor density close to the center of the linearity volume, whereas the correction coil exhibits its largest conductor density at the edges of the linearity volume.

In a second embodiment, the second sub-coil is fashioned as an amplification coil according to FIG. 9, for example. Its main task is to change, particularly to increase, the gradient intensity of the gradient field generated by the first sub-coil. For this purpose, the amplification coil has a coefficient $A_{2(1,0)}$, which exhibits a value that is unequal to zero corresponding to a desired amplification, for example.

In the case of a gradient coil arrangement (second embodiment) that is not actively shielded, it is possible, in contrast to the first embodiment that two winding planes may be necessary according to FIG. 9, for example. This is because not only the first sub-coil but also the second sub-coil exhibit their highest conductor density close to the center of the linearity volume.

This is correspondingly valid for other gradient coil arrangements such as transverse gradient coil arrangements. Mixed types between pure correction coils and amplification coils can also be fashioned in other embodiments.

According to the invention, optimization tasks containing target functions and secondary conditions are set up and solved for determining current adjustments in the sub-coils of aforementioned gradient coil arrangements to adjust certain properties of the gradient field. The basic procedure is always the same. Subsequently, an optimization task including its target function and secondary conditions for optimizing the linearity of the gradient field is described in greater detail.

For a longitudinal gradient coil with a number N of sub-coils, with fixed rated currents $I_{nv}$ and with coefficients $A_{v(l,0)}$ that are fixed by an embodiment of the sub-coils, the quality of the linearity of the gradient field can be described with the following target function Q:

$$Q = \sum_{l=0}^{\infty} k_l \sum_{v=1}^{N} \frac{l_v}{l_{nv}} \cdot A_{v(l,0)}$$

The index v designates the v-th sub-coil and the factors $k_l$ are weighting factors. In order to optimize the linearity of the gradient field, the weighting factor $k_1$ is to be selected equal to zero, since the gradient intensity of the gradient field, which is not to be optimized, is described by the appertaining coefficient $A_{v(1,0)}$. Further weighting factors such as $k_2$, $k_5$, $k_7$ etc. are weighted with a value between zero and one corresponding to their interference effect with respect to the magnetic resonance imaging. The value one signifies a high weighting, i.e., this interference order has a particularly disturbing effect. The value zero correspondingly means that the interference order weighted therewith is irrelevant.

The target function Q is minimized by means of a variation calculation, for example under the following secondary conditions. Given a fixed maximal slew rate of a selected sequence, the maximum of the magnetic flux density $B_z (r, \theta, \phi)$ of the gradient field must be smaller than a specific limiting value, which is proportional to a stimulation threshold, so that stimulations are avoided during the execution of the sequence. Furthermore, the gradient intensity is to be larger than a limiting value determined by the sequence. Moreover, the sub-coil currents $I_v$ are not allowed to exceed fixed limiting values such as the reference currents $I_{nv}$ in the v-th sub-coils.

For example, it is advantageous, with respect to the variation calculation for minimizing the target function Q, to represent the currents in the N sub-coils in vector notation and to represent the coefficients in a corresponding coefficient matrix. Then, the target function Q is minimized by an approximate matrix inversion, for example by means of a square simplex algorithm, and the currents to be adjusted in the sub-coils derive.

As an exemplary embodiment of the invention in the form of a flow chart, FIG. 13 shows how the previously described continuous adjustment of properties of a gradient field is integrated into a magnetic resonance tomography imaging procedure described by the steps 131 to 136. In a first step 131, a user initially selects a sequence type such as a spin echo or an echo planar sequence. In step 132, a corresponding sequence program is subsequently loaded. In step 133, allowable adjustment ranges of the sequence parameters are determined. For this purpose, a calculation module A is called, which, dependent on the selected sequence type, receives fixed minimum requirements with respect to the properties of the gradient field such as linearity, gradient intensity and slew rate. For example, on the basis of the previously explained equations and steps, the calculation module calculates the allowable adjustment ranges therefrom, for example for the field of view FOV and for the repetition time TR, so that the selected sequence type with sequence parameters within the adjustment ranges can be executed by the gradient system of the device. A secondary condition is that no stimulations are initiated during the execution. For example, the linearity deviation of the gradient field can be offered as an additional sequence parameter. In step 134, the user selects the sequence parameters within the adjustment ranges. Subsequent to the selection of the sequence parameters in step 134 and prior to the execution of the sequence in step 136, the device hardware is prepared in step 135, in order to fill look-up tables, for example. During this preparation, a calculation module B is called, which, on the basis of the selected sequence parameters, calculates the corresponding current intensities and current directions for each sub-coil of the gradient system such that a fixed stimulation threshold is not exceeded. If—despite the allowable adjustment ranges—sequence parameters were fixed, which cannot be executed by the gradient system or which cannot be executed without stimulations, the calculation module B provides a corresponding message.

Sequences referred to as realtime sequences are characterized by having sequence parameters that can be modified, for example by the user, during the execution of a sequence. For example, it is thus possible to modify an orientation of a tomogram from image to image and/or the image resolution, which, as is known, is directly influenced by the gradient intensity. A realtime sequence is executed according to a pipeline architecture (shown in FIG. 14). For example, a first image B1 passes through the three steps data acquisition, raw data processing and visualization during the time course. During the data acquisition for the image B1, the user, for a second image B2, which is to be acquired after the image B1 has been acquired, can modify the sequence parameters, in the framework of an interactive device inquiry, for the image B2 relative to the image B1 within the allowable adjustment ranges. This is also valid for further images. The calculation module B of FIG. 13 becomes active regarding each modification of sequence parameters from one image to the next and determines the corresponding current adjustments of the gradient system. In realtime sequences containing functional tasks, such as diffusion encoding, the intensity of the diffusion weighting is offered as an additional changeable sequence parameter.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a magnetic resonance tomography apparatus having a gradient system with at least one gradient coil arrangement for generating a gradient field in a spatial direction, said gradient field having gradient field properties, and having an energy supply device connected to the gradient coil arrangement, and said gradient coil arrangement including at least one first sub-coil and one second sub-coil, said method comprising the steps of:

via said energy supply device, adjusting respective currents in said first sub-coil and said second sub-coil independently of each other; and continuously adjusting at least one of said gradient field properties by determining and setting the current in at least one of said first and second sub-coils by solving an optimization task containing a target function and at least one secondary condition for avoiding stimulations in a living examination subject in said tomography device.

2. A method as claimed in claim 1 wherein one of said gradient field properties is magnetic flux density of said gradient field, and wherein said magnetic resonance tomography apparatus is operated with a sequence having a fixed slew rate, and wherein said method comprises the additional step of avoiding said stimulations by maintaining an extreme value of said magnetic flux density of said gradient field below a limiting value given said fixed slew rate.

3. A method as claimed in claim 1 comprising solving said optimization task by a variation calculation.

4. A method as claimed in claim 1 wherein one of said properties of said gradient field is magnetic flux density, and wherein said method comprises employing a function as said target function that contains coefficients for a spherical development of said magnetic flux density of said gradient field.

5. A method as claimed in claim 4 comprising employing a function as said target function that contains coefficients for each of said sub-coils.

6. A method as claimed in claim 5 comprising multiplying the respective coefficients for at least one of said sub-coils with a factor corresponding to a ratio of an adjustable current in said one of said sub-coils to a nominal current in said one of said sub-coils.

7. A method as claimed in claim 6 comprising employing a further secondary condition that at least one of the coefficients multiplied by said factor is greater than a fixed limiting value.

8. A method as claimed in claim 1 comprising the additional step of additionally determining at least one of said properties of said gradient field by setting a sequence parameter in a sequence for operating said tomography device.

9. A method as claimed in claim 8 comprising restricting selection of said at least one of said sequence parameters to a range for a selected sequence type, so that the selected sequence can be executed by said gradient system.

10. A method as claimed in claim 9 comprising limiting said at least one sequence parameter to a range for a fixed stimulation limiting value, for preventing said stimulations during execution of said sequence.

11. A method as claimed in claim 8 comprising modifying said sequence parameter during said sequence.

12. A method as claimed in claim 1 wherein said gradient field properties include linearity and wherein the step of continuously adjusting at least one of said properties of said gradient field comprises continuously adjusting said linearity.

13. A method as claimed in claim 12 comprising adjusting the current in said first sub-coil to set said linearity of said gradient field, and controlling the current in said second sub-coil to continuously modify said linearity.

14. A method as claimed in claim 1 wherein said gradient field properties include linearity volume and wherein the step of continuously adjusting at least one of said properties of said gradient field comprises continuously adjusting said linearity volume.

15. A method as claimed in claim 14 comprising adjusting the current in said first sub-coil to set said linearity volume of said gradient field, and controlling the current in said second sub-coil to continuously modify said linearity volume.

16. A method as claimed in claim 1 wherein said gradient field properties include gradient intensity and wherein the step of continuously adjusting at least one of said properties of said gradient field comprises continuously adjusting said gradient intensity.

17. A method as claimed in claim 16 comprising adjusting the current in said first sub-coil to set said gradient intensity of said gradient field, and controlling the current in said second sub-coil to continuously modify said gradient intensity.

18. A method as claimed in claim 1 wherein said energy supply device has a first gradient amplifier and a second gradient amplifier, and comprising the steps of connecting said first gradient amplifier to said first sub-coil and connecting said second gradient amplifier to said second sub-coil.

19. A method as claimed in claim 1 wherein said properties of said gradient field include linearity volume, and wherein said method comprises the steps of physically designing said first sub-coil to set a specific linearity volume of said gradient field, and using said second sub-coil as a correction coil for modifying said specific linearity volume.

20. A method as claimed in claim 1 wherein said properties of said gradient field include linearity, and wherein said method comprises the steps of physically designing said first sub-coil to set a specific linearity of said gradient field, and using said second sub-coil as a correction coil for modifying said specific linearity.

21. A method as claimed in claim 1 wherein said properties of said gradient field include linearity volume and linearity, and wherein said method comprises the steps of physically designing said first sub-coil to set a specific linearity volume and linearity of said gradient field, and using said second sub-coil as a correction coil for modifying said specific linearity volume and linearity.

22. A method as claimed in claim 1 wherein said properties of said gradient field include gradient intensity, and wherein said method comprises the steps of physically designing said first sub-coil to set a specific gradient intensity of said gradient field, and using said second sub-coil as an amplification coil for modifying said specific gradient intensity.

23. A method as claimed in claim 22 comprising using said second sub-coil as an amplification coil for increasing said specific gradient intensity.

24. A method as claimed in claim 22 comprising physically designing said first sub-coil to set a specific gradient intensity which has a maximum amplitude.

* * * * *